US007560715B2

United States Patent
Pedroni (10) Patent No.: US 7,560,715 B2
(45) Date of Patent: Jul. 14, 2009

(54) SYSTEM FOR THE DELIVERY OF PROTON THERAPY

(75) Inventor: Eros Pedroni, Brugg (CH)

(73) Assignee: Paul Scherrer Institute, Viligen (CH)

( * ) Notice: Subject to any disclaimer, the term of this patent is extended or adjusted under 35 U.S.C. 154(b) by 264 days.

(21) Appl. No.: 11/587,832

(22) PCT Filed: Feb. 19, 2005

(86) PCT No.: PCT/EP2005/001742

§ 371 (c)(1), (2), (4) Date: Oct. 26, 2006

(87) PCT Pub. No.: WO2005/102453

PCT Pub. Date: Nov. 3, 2005

(65) Prior Publication Data

US 2008/0023644 A1    Jan. 31, 2008

(30) Foreign Application Priority Data

Apr. 27, 2004 (EP) .................... 04008190
Jul. 22, 2004 (EP) .................... 04017266

(51) Int. Cl.
    *H01J 3/32*    (2006.01)
    *G21G 1/10*    (2006.01)
(52) U.S. Cl. ............... 250/492.3; 250/398; 250/505.1; 250/492.1; 315/501; 315/507
(58) Field of Classification Search ......... 250/491.1, 250/492.3, 396 ML, 505.1, 298, 400
    See application file for complete search history.

(56) References Cited

U.S. PATENT DOCUMENTS 6,034,377 A     3/2000  Pu
6,476,403 B1 *  11/2002 Dolinskii et al. ......... 250/492.3

(Continued)

FOREIGN PATENT DOCUMENTS

EP        0 911 064 A2    4/1999

(Continued)

OTHER PUBLICATIONS

Pedroni et al.; "The 200-MEV Proton Therapy Project at the Paul Scherrer Institute: Conceptual Design and Practical Realization"; Medical Physics, American Institute of Physics, New York, US; vol. 22, No. 1, 1995, pp. 37-53; XP-000505145; ISSN: 0094-2405, p. 46.

(Continued)

*Primary Examiner*—Nikita Wells
*Assistant Examiner*—Johnnie L Smith
(74) *Attorney, Agent, or Firm*—Laurence A. Greenberg; Werner H. Stemer; Ralph E. Locher (57) ABSTRACT

A process for an intensity-modulated proton therapy of a predetermined volume within an object includes discretising the predetermined volume into a number of iso-energy layers each corresponding to a determined energy of the proton beam. A final target dose distribution is determined for each iso-energy layer. The final target dose distribution or at least a predetermined part of this final target dose distribution is applied by parallel beam scanning by controlling the respective beam sweepers, thereby scanning one iso-energy layer after the other using an intensity-modulated proton beam while scanning a predetermined iso-energy layer.

12 Claims, 5 Drawing Sheets

U.S. PATENT DOCUMENTS

| | | | |
|---|---|---|---|
| 6,891,177 B1 * | 5/2005 | Kraft et al. | 250/505.1 |
| 7,154,108 B2 * | 12/2006 | Tadokoro et al. | 250/492.3 |
| 7,247,869 B2 * | 7/2007 | Tadokoro et al. | 250/492.3 |
| 7,317,192 B2 * | 1/2008 | Ma | 250/396 ML |
| 2003/0164458 A1 * | 9/2003 | Eickhoff et al. | 250/491.1 |

FOREIGN PATENT DOCUMENTS

| | | |
|---|---|---|
| EP | 0 986 070 A1 | 3/2000 |

OTHER PUBLICATIONS

Pavlovic; "Beam-optics study of the gantry beam delivery system for light-ion cancer therapy"; Nuclear Instruments & Methods in Physics Research, Section—A: Accelerators, Spectrometers, Detectors and Associated equipment, North-Holland Publishing Company, Amsterdam, NL; vol. 399, No. 2-3, Nov. 11, 1997, pp. 439-454; XP-004095517; ISSN: 0168-9002, p. 442, left-hand column, figures 1,2.

* cited by examiner

SYSTEM FOR THE DELIVERY OF PROTON THERAPY

BACKGROUND OF THE INVENTION

The invention relates to a system and a method for applying an intensity-modulated proton therapy on a predetermined tumor volume within the body of the patient.

The number of new hospital-based facilities for charged particles therapy is growing quickly, especially in Japan and in the USA. Proton therapy is becoming a realistic therapeutic possibility for treating well-selected cancer types in centralized large hospitals.

All new commercial systems are based on the passive scattering technique. The compact gantry for proton therapy at the Swiss Paul Scherrer Institute (PSI) is still the only facility in the world using a dynamic beam delivery technique based on the active scanning of a small proton pencil beam. Only at the German GSI facility (GSI=Gesellschaft fur Schwerionenforschung, Darmstadt) is a similar beam delivery technique used, with carbon ions in a horizontal beam line. By using this modern approach to radiation therapy the conformal shaping of the dose is achieved just by computer control without the need of field specific hardware.

This approach to proton therapy is attracting more and more the interest from industry and hospitals internationally, because this method is now being recognized as the preferred method for providing intensity-modulated radiation therapy (IMRT) using proton beams, a technique now known in the community as intensity-modulated-proton therapy (IMPT). This technique (based on the modulation of the totally delivered beam fluence) should not be confused with the active dynamic control of the beam intensity (the instantaneous dose rate) described later below. In contrast to photon-IMRT, with proton beam scanning one can control independently the flux, the range, the position and direction of each proton pencil beam, making use of all available degrees of freedom including the depth of penetration of the proton beam into the patient. With this method similar results can be obtained as with IMRT but with improved conformity and with a significant reduction (by a factor of two or three) of the dose burden on the healthy tissues surrounding the tumor.

The practical feasibility of IMPT was demonstrated recently at PSI by applying this new technique to a few of the clinical cases treated on the PSI Gantry 1.

Subsequently, the main features of the existing PSI Gantry 1 are described to recall the strengths and the weak points of the present system.

The PSI Gantry 1 is operational since 1997. By the end of 2003 166 patients have been treated with this system, with tumors located mainly in the skull, spinal cord and in the low pelvis. Currently up to 17 patients are treated per day. The preliminary clinical results obtained by using the new beam scanning technique are very encouraging.

The positive aspects achieved with the present system, PSI Gantry 1, are:
a) the possibility to apply conformal therapy with variable modulation of the range delivered "all by computer" without the need to use field specific beam shaping devices like collimators and compensators;
b) the capability to apply multiple fields without the personnel entering the treatment room; and
c) the capability to deliver IMPT (presently only on well immobilized targets).

The concepts for this system are now more than 13 years old, the system was built with limited resources, only for the goal of showing the feasibility of scanning. For a better understanding of the technical improvements introduced by the inventions for the PSI Gantry 2 the main technical features of the PSI Gantry 1 are briefly given below:

The patient table is mounted eccentrically on the PSI Gantry 1 and rotates with the gantry. A counter-rotation maintains the patient table horizontal at any time. This choice was dictated by the limited amount of space available for the gantry. Without pushing the compactness of the system down to only 4 m diameter it would not have been possible to build such a Gantry 1 system at PSI. The eccentric mounting of the patient is now the most often criticized point, since the patient table moves away from the floor and the patient couch is not accessible to the personnel when the proton beam is applied from below.

The beam delivery used on Gantry 1 is a "discrete" spot scanning method (a "step-and-shoot" method), based on maximum simplicity. A proton pencil beam with a Gaussian profile of 7-8 mm FWHM is used and the beam is scanned in steps of 5 mm. The beam flux is measured with parallel plate ionization monitors in front of the patient. The beam is switched off during the displacement of the beam in-between spots with a kicker magnet. The most often used scan motion is done with a sweeper magnet installed upstream of the last 90° bending magnet. The beam optics is designed such that the action of the sweeper results in a parallel displacement of the swept beam in the patient. The magnetic scanning is applied on Gantry 1 only in one lateral direction, in the dispersive plane of the gantry (the direction U along the gantry axis). A range shifter system is used in front of the patient for providing fast changes of the penetration depth of the beam (second direction S of scanning, in depth). The range shifter consists of a stack of 5 mm-thick polyethylene plates, which are moved sequentially into the beam by pneumatic valves. The motion of the patient table is used as the third axis of scanning. This is the slowest and most seldom used motion, which is applied in the transverse non-dispersive direction T. The whole is a Cartesian beam scanning system.

The points to be improved on an inventive system and an inventive method in comparison to the present system are: The unsatisfactory access to the patient table when the beam is applied from below. The slow speed of scanning, due to the chosen sequence of the scanning devices, magnetic $1^{st}$, range $2^{nd}$ and table $3^{rd}$. The use of two mechanical systems makes the scan too slow for applying repeatedly target repainting. The scanning on Gantry 1 is therefore quite sensitive to organ movements.

Further, a system for an intensity-modulated proton therapy of a predetermined volume within an object is known in the prior art, comprising:
a) a proton source in order to generate a proton beam being adjustable with respect to the beam intensity;
b) a degrader being optionally disposed in the proton beam in order to attenuate the energy of the protons in the proton beam to a desired proton energy in the proton beam;
c) a number of proton beam bending and/or focusing units constituting the beam line for the transport of the beam, where a section of the beam line can be rotated around the patient table (the actual proton gantry);
d) a beam nozzle on the gantry having an outlet for the proton beam to penetrate the predetermined volume of the object;
e) a beam bending magnet being disposed upstream of the nozzle; and
f) a couple of sweeper magnets being disposed upstream of said beam bending magnet in order to sweep in a parallel fashion the proton beam in both lateral direction at the exit of the last beam bending magnet.

The method to deliver the dose by a double magnetic scanning and by changing the beam energy is known.

SUMMARY OF THE INVENTION

However, the innovations, which are protected by this application, are related to particular aspects of the system and of the beam delivery method described in the cited publication. The innovations can be summarized in the following list:

The first part of the invention regards the optimized system design. An inventive system for an intensity-modulated proton therapy of a predetermined volume within an object comprises:

a) a proton source in order to generate a proton beam (B) being adjustable with respect to the beam intensity;
 b) a degrader being optionally disposable in the proton beam (B) in order to attenuate the energy of the protons in the proton beam (B) to a desired proton energy in the proton beam (B);
 c) a number of proton beam bending and/or focusing units;
 d) a beam nozzle (N) having an outlet for the proton beam (B) to penetrate the predetermined volume (T) of the object (M);
 e) a beam bending magnet (A3) being disposed upstream of the nozzle (N); and
 f) a couple of sweeper magnets (WT, WU) being disposed upstream of said beam bending magnet (A3) in order to sweep the proton beam (B) in both lateral directions (T, U) before the proton beam (B) enters into the beam bending magnet (A3), characterized in that g) said beam nozzle (N) is defining a cross-sectional scanning area (SF) substantially perpendicular to the proton beam (B) in the range of 10 to 30 cm$^2$, and
 h) said sweeper magnets (WT, WU) and said beam bending magnet (A3) are controlled in order to guarantee a parallel beam orientation over the complete cross-sectional scanning area (SF).

The use of a reduced range of magnetic scanning—on a small compact nozzle and a small air gap to the patient allow to design a very compact gantry which brings an almost unscattered (due to the short distance) proton beam into the target volume. The use of the two-dimensional parallelism of scanning—for the field size extension using the patient table on the basis of a "geometrical" field patching—which opens up the option to use a slow continuous table motion during multiple target rescannings in order to compensate the comparably small cross-sectional scanning area at the nozzle.

The possibility, by virtue of the design of the beam optics, to scan the beam in two dimensions while keeping the direction and the shape of the beam unchanged (parallel beam scanning) is a major characteristics of the PSI Gantry 2. Strong emphasis is given on the utilization of this important feature. The parallelism of scanning can be used for extending the range of beam scanning beyond the given magnetic scanning range, by combining it with the patient table motion in a simple procedure, which is independent of treatment planning ("geometrical" field patching). While using a geometrical field patching technique the patient table can be moved very slowly and continuously, by compensating the displacement of the table motion with an offset applied to the sweepers (field patching applied with continuous table motion). This approach is very attractive especially in the context of multiple target repaintings, which are needed in the presence of organ motion (slow table motion during multiple target repaintings). The geometric field patching method allows overcoming the problems posed by a limited range of magnetic scanning. This feature can then be used for designing a nozzle which is small in size in both transverse directions to the beam (slim very compact nozzle) as given by the defined size of the cross-sectional scanning area. The use of a slim nozzle is the preferred solution for placing the patient very close to a pre-absorber system and to the beam monitors, both enclosed in the nozzle (small air gap to the patient), without colliding with patient shoulders, to avoid the broadening of the beam due MCS in the air gap to the patient.

According to the inventive process for an intensity-modulated proton therapy of a predetermined volume within an object (M); the following steps are comprised:

a) dividing the predetermined volume (T) into a number of iso-energy layers (L) each corresponding to a determined energy of the proton beam (B);
 b) determining a final target dose distribution for each iso-energy layer (L); and
 c) applying the final target dose distribution or at least a predetermined part of this final target dose distribution by parallel beam scanning under controlling the respective beam sweepers (WT, WU), thereby scanning one iso-energy layer (L) after the other using an intensity-modulated proton beam (B) while scanning a predetermined iso-energy layer (L).

Therefore, it is now possible to perform the magnetic scan (at each iso-energy layer) along the target contour (at that proton depth) and on similar equidistant contours in the interior of the target (contoured double magnetic scanning). The concentric contours are scanned with close-to-maximum speed by shaping the dose using the beam intensity modulation controlled at the ion source of the accelerator. By this method scanning speed is gained and thus a large amount of target repaintings can be applied. Additionally, the best possible quality of the lateral fall-off of the dose distribution at the edge of the field can be obtained and the dynamics for the beam intensity variations can be kept low, while working with maximum speed of scanning. By virtue of the 1:1 imaging of the beam optics of Gantry 2 from the coupling point of the gantry to the isocenter, an imaged (virtual) collimation on the scanned beam spots can be applied by using a (real) collimator block (moving radially and azimuthally) at the coupling point of the gantry (contoured double magnetic scanning with imaged collimation applied to a scanned broad beams).

All these points are explained in more details below.

BRIEF DESCRIPTION OF THE SEVERAL VIEWS OF THE DRAWINGS

Examples of the invention are hereinafter described with reference to the drawings. In the drawings.

DETAILED DESCRIPTION OF THE INVENTION

Figure 1:
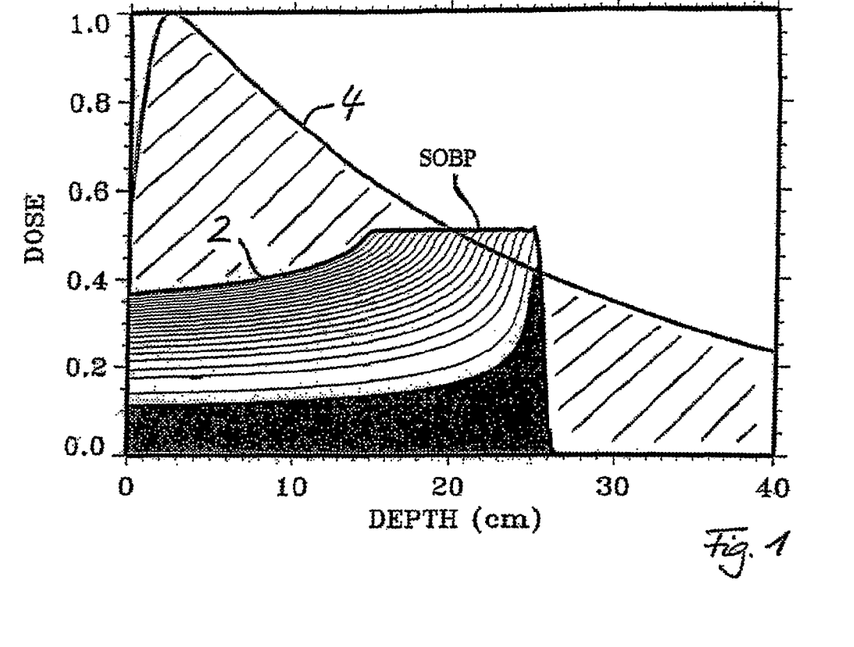
FIG. 1 is a schematic diagram of the depth dose distribution of protons in comparison to the photons; the Bragg peak is usually modulated in depth through the stacking of pencil proton beams of different energies and fluence to obtain a spread-out-Bragg-peak (SOBP)

FIG. 1 shows a schematic diagram of the depth dose distribution of protons (graph 2) in comparison to the depth dose distribution of photons (graph 4) in human tissue equivalent material. The advantage of proton therapy is given by its superior physical selectivity, which allows to design a plateau SOBP (the so-called spread out Bragg peak) for the dose in a distinct depth of the target volume which is located within the patient. Protons have a well-defined penetration range in biological tissue and they deposit the maximum of their energy in the region where they stop. This gives rise to the so-called Bragg peak, which is shown in FIG. 1 as the dose deposition of a mono-energetic proton beam as a function of depth. This must be compared with clinical photons, which have a characteristic exponential fall-off of the dose (graph 4).

Due to their electric charge protons offer the possibility to localize the dose not only in the lateral directions by the magnetic scanning technique but also as a function of the depth. Compared to photons, with protons a remarkably reduction of the integral dose outside of the target volume is achieved, i.e. by a factor of 2 to 5 depending on the specific case (savings on insane tissue treatment being indicated by the hatched areas in FIG. 1).

FIG. 1 depicts also how a spread out Bragg peak SOBP can be obtained through the stacking of pencil proton beams having different ranges and intensities. A homogenous dose distribution in depth can be thus constructed from a single beam direction (with photons one needs several beam directions). One can easily imagine that this technique allows to design rather complicated three-dimensional target volume dose distributions which can be achieved by magnetic scanning of the proton beam in both lateral directions and by energy scanning in depth.

Figure 2:
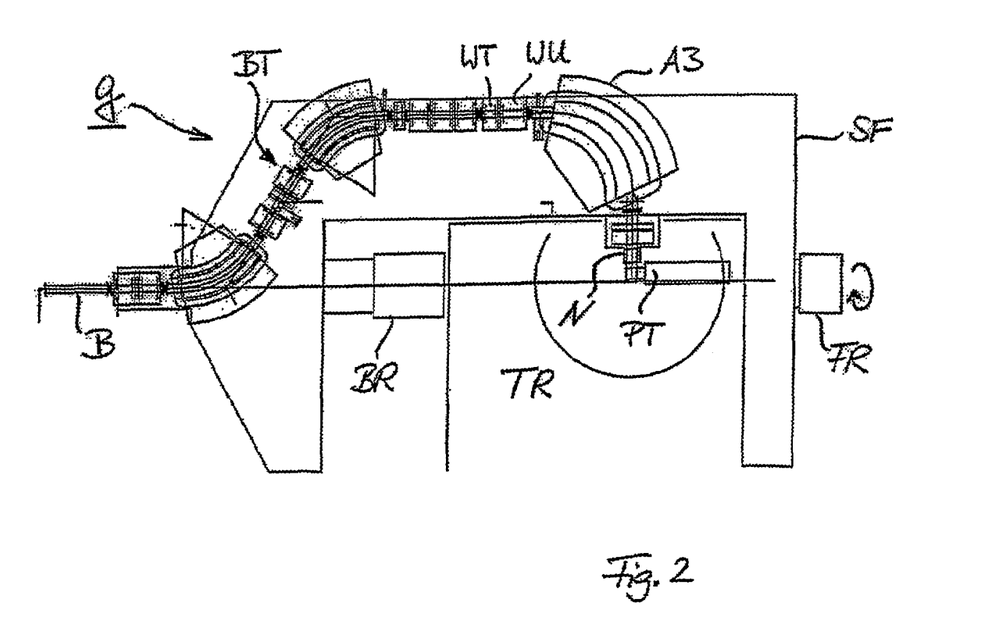
FIG. 2 is a schematic diagram of a gantry cross section.

FIG. 2 is a schematic top view on the cross section of a gantry G for the illustration of its mechanical layout. A proton beam B is generated in a non-illustrated accelerator, such as a cyclotron (but synchrotron, linear accelerator or others are possible as well), which is adjustable with respect to the intensity of the beam B. For directing the beam B to an object, such as a patient or a biological probe volume, a beam transport system BT is installed within a support frame SF. The support frame SF is pivoted with a front roll FR and a back roll BR. The beam transport system BT is supposed to rotate only on one side of the gantry G by ±95°. Therefore, a patient table PT is mounted independently from the gantry G and is accessible from one side of the treatment room TR which enables the medical personal to access to the patient at any time through a permanent fixed floor.

Further, medical equipment favorable to the medical therapy, like CT, anesthesia devices etc. can be disposed at any time very close the patient table PT. A nozzle N located utterly downstream of the beam transport system BT can be located very close to the patient, too, achieving remarkably benefits to the sharpness of the proton beam B in the target volume. From the patient table PT, the patient experiences the treatment room TR more or less as a room having normal dimensions with a small rotating nozzle N with a sliding cover extending inside this treatment room TR. The patient sees only the nozzle N rotating along a slit in the half cylindrical internal wall of the treatment room TR. With this design the need of a moving floor (except for the slit of the nozzle N) is canceled. The treatment room TR has for example a length of 6 to 7 m, depth of 5 to 6 m and a height of 2.2 to 2.4 m. These dimensions of the treatment room TR even facilitates the horizontal rotation of the patient table PT along its horizontal axis.

Figure 3:
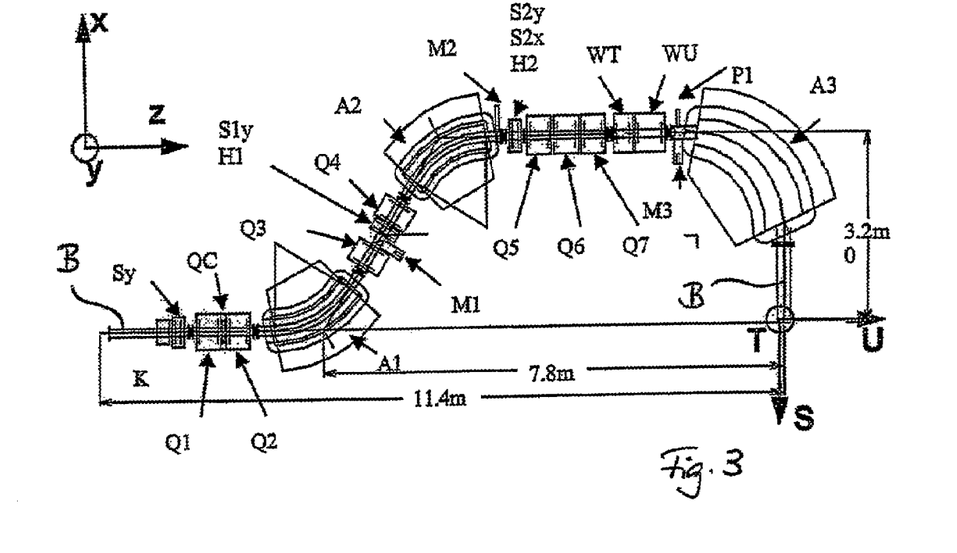
FIG. 3 is a schematic diagram of the beam optical components.

The beam transport system BT used for the application of the proton beam B to the target volume within a patient is schematically shown in FIG. 3. This beam transport system BT comprises a system of three dipoles A1, A2, A3 and seven quadrupols Q1 to Q7. Other elements are steering magnets Sx/y (some of those elements are embedded as separate windings in the sextupoles H), optional slits or fixed collimators K, beam diagnostic elements M and vacuum pumps P. The main dynamic elements for the scanning are the two sweeper magnets WU and WT and a dynamic quadrupole corrector QC.

The beam optics calculations were performed for a nominal beam energy of 230 MeV (other energies are obtained by scaling the electric current in the magnetic elements of the beam line according to the momentum of the beam). The bending radius applied to the beam B is chosen to 1.5 m. The nominal field is B=1.5 Tesla. The radial parallel displacement of the beam line from the rotation axis is about 3.2 m. The distance of the exit field boundary of the 90° bending magnet to the isocenter is approx. 1.7 m. This space available in this embodiment is sufficient for keeping the bulk of the 90° bending magnet A3 during rotation to stay outside of the treatment room TR at a distance of about 1.2 m from the isocenter, in order to keep the ceiling of the treatment room TR at least 2.4 m high (normal room height) which is a significant improvement for the mental well-being of the patient. The shape of the beam line is derived from these settings, by using the minimal space necessary to place all beam transport elements needed to fulfill the beam optics requirements inside the most minimal space of the support frame SF. This beam transport system BT offers therefore the full parallelism of the beam B during painting, a true size imaging from the starting point of the rotating beam line (gantry coupling point) to the isocenter (the end point where the beam is scanned in the patient). Further, beam achromatism and beam focus invariance during double sweeping in U- and T-direction is achieved.

The beam delivery elements disposed upstream of the beam transport system BT are not shown. A cyclotron delivers a continuous beam being adjustable with respect to its intensity. The change of the energy will be preferentially done by changing dynamically the setting of a degrader and the tune in the beam line ahead and on the gantry G. Between the cyclotron and the degrader a fast kicker magnet is mounted for the switching ON and OFF of the proton beam B with a reaction time of only 50 μs.

Figure 4:
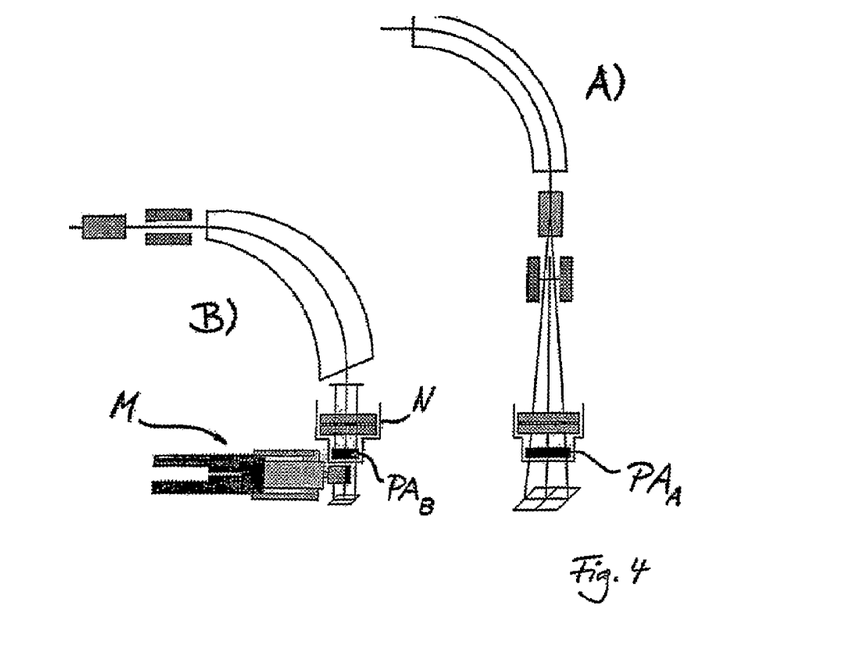
FIG. 4 is the comparison in a schematic layout of a long throw gantry (on the right—solution A) compared with a compact gantry (on the left—solution B)

FIG. 4 shows the main difference of the PSI solution compared to the more usual solution to place the scanning magnets after the last bending magnet. The most usual approach is to place in the layout of the beam line of the gantry, the sweeper magnets (or scattering devices) after the last bending magnet (solution A, adopted for all proton gantries proposed or realized so far, except for the Gantry 1 of PSI). In this case, a long drift space (throw) is required between the sweeper magnets and the isocenter, in order for the lateral spread of the beam to take place. The drift space is thus added to the radius of the gantry. The beam impinges in the patient with varying divergence. The shorter the throw, the stronger is the bending power needed for the sweeper magnets and the stronger is the divergence of the beam. Usually, one chooses a distance of 1.5-2 m and for the lateral extent of the scan a maximum width of the scanned region of typically 30 cm×40 cm.

By placing the sweepers before the last bending magnet the radius of the gantry (to 7.5 m for an iso-centric layout like the new Gantry 2 of PSI) can be tremendously reduced since the drift space is included in the path of the beam in the last bending magnet (solution B, left side of FIG. 4). Thus, a significantly more compact gantry system is achieved.

The only "drawback" in this last solution is that the range of scanning is limited by the gap and the width of the poles of the last bending magnet A3, which must be wide enough to contain the scanned beam to the exit of this beam element. This implies that the applicable range of scanning is somewhat reduced and that the power consumption for the last bending magnet A3 is higher as for a solution of the type A.

If the geometrical shape and the magnetic field of the last bending magnet A3 is designed very carefully, the beam can be scanned in a parallel fashion in two dimensions (to keep the apparent source of the protons at the infinite) at the given cross-sectional area. The idea to provide the parallelism of the scanned beam in both directions is well known in the field, since it was realized at least in one dimension already on the PSI Gantry 1. New is however the proof through detailed beam optics calculations (as shown in the proposal for Gantry 2), that this method is indeed possible also for a two-dimensional scan.

The advantages of having a parallel scanned beam are summarized in the following:

With solution B we simplify treatment planning, since the calculation is applied on a simple Cartesian grid.

The verification dosimetry is also simpler and less prone to errors. We are not sensitive to the longitudinal positioning of the dosimetric equipment and of the patient along the beam direction (the distance d of the object to the apparent source of the protons produces otherwise, in a divergent system, a "one over d-squared" dependent effect on the dose, an effect well-known from conventional therapy). Additionally, with a parallel scan less skin dose outside of the target volume is applied.

If one uses collimators (as optional devices in addition to scanning), one can machine the edges of the collimators with simple normal cuts. With solution A one needs to apply a conical cut on the internal face of the collimator hole to compensate for the divergence of the beam, another problem known from conventional therapy).

A major advantage often not recognized in the proton therapy field (mainly because only PSI has up to now some practical experience of using scanning on a gantry) is however the potential for applying patching field techniques, for extending "on line" the range of magnetic scanning.

The parallelism of scanning makes the patching of dose fields very easy. One can keep the range of magnetic scanning quite small (typically in the range of 150 to 300 cm², i.e. of only 20 cm×10 cm). The delivery of the dose is however calculated in treatment planning as if the range of magnetic scanning would be unlimited. Since the beam is maintained parallel to its nominal beam direction we don't need to decide in the dose calculation, where the beam and the patient table will be exactly positioned in practice during treatment; magnetic parallel scanning and table motions are in principle freely interchangeable. The dose depends only on the final position of the beam with respect to the patient body, we can thus postpone the decision on how to move the patient table in combination with the sweepers magnets to the last instant during beam delivery (the patient table is used here as a device for extending "on-line" the range of scanning).

The same is not true for a system with an inherent divergence. With a scattered (necessarily divergent) beam it is not possible to combine dose fields delivered at different table positions without destroying the homogeneity of the resulting dose distribution (with unavoidable dose errors in the overlapping region of the fields). With a divergent scanning system one can in principle combine several fields applied at different table positions into a homogenous dose, since one has all the degrees of freedom to modify the dosage of each single beam spot. This must however be implemented already in the optimization procedure in the dose calculations during the phase of treatment planning (the field patching must be part of the actual planning). This is probably one of the reasons, why the range of magnetic scanning for the systems of the type A is usually chosen to be very large, enough to cover all possible target sizes. The puzzling question with those systems is however: which may be in practice the maximum target size that can reasonably be considered?

With a parallel scanned beam, we gain in principle the freedom to simply extend the range of scanning beyond the chosen magnetic range, and to treat virtually any target size, just be shifting the patient table, independently of therapy planning.

One important advantage of the present invention is the idea to take the maximum advantage from the possibility to use a parallel scanned beam. The combined use of magnetic scanning and table motion permits to extend the range of scanning beyond any practical limits (to treat for example medulloblastoma cases, which are cranio-axial spinal irradiation of children extending over a range of up to 80 to 90 cm length, just in one go).

The basic patching technique is performed in its simpler form as following:

a) if a large target volume is bigger than the range of scanning, the matrix of beam spots will be separated in partially overlapping sub-volumes (concept of "patched" dose fields, addition of constituent dose fields)

b) each subvolume is chosen small enough to be covered by the (limited) range of magnetic scanning c) the dose is delivered on each subvolumes at different body positions by moving the patient table d) each subvolume is usually irradiated including energy changes, i.e. as a fully painted dose volume e) in the overlapping region between sub-volumes the constituent dose fields are applied with opposed smooth dose transitions (a gradual dose fall-off of field 1 compensated by the corresponding rising of the dose of field 2) in order for the method to be less sensitive to organ motion errors. The manipulation of the fall-off is very simple since it is realized by a linear reduction (in the overlapping region) of the required dosage of each spot.

The gantry solution B allows a fast double magnetic scanning on a more compact gantry.

This compact gantry having diameters in the range of 4 m (eccentric) to 7.5 m (isocentric) must keep reasonably small the pole size and the air gap, the weight and power consumption of the last beam bending magnet A3.

This yields on the other hand in a lower power consumption for the sweepers WU, WT, delivering a comparably faster speed of scanning.

The fast speed of scanning is accessible due to the chosen sequence of the scanning devices now double magnetic $1^{st}$ and $2^{nd}$ with range or energy $3^{rd}$, and with the additional movement of the table for treating large fields. The use of a fast double magnetic scanning system makes the scan fast for applying repeatedly target repainting (typically 10 times) and facilitates the scanning even under quite sensitive organ movements.

Option to move the table continuously for treating large fields with multiple repainted volumes In the context of repeatedly applied volumetric target rescannings, the table can be moved very slowly in a continuous fashion during beam delivery. Since the direction and the dose characteristics of each pencil beam are all maintained invariant, any ongoing small table movement can be equivalently corrected with a similar sweeper motion in the opposite direction. While the beam is delivered as a partial volume in a grid we can freely move the table. The effectively displaced position of the patient due to the movement of the table is known at any instance and can be immediately corrected as an offset applied to the sweepers.

Figure 5:
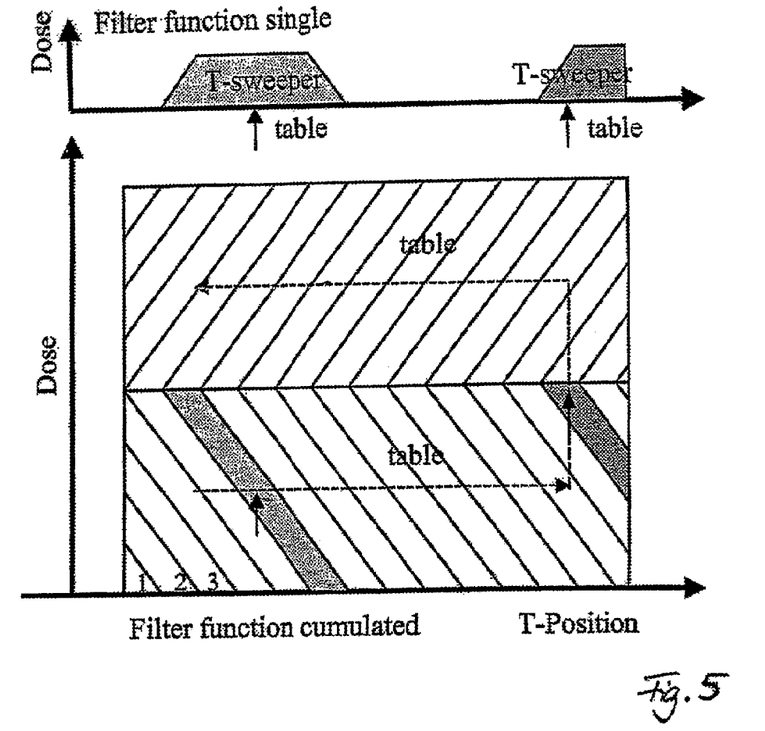
FIG. 5 is a functional diagram of the table movement in order to patch fields for larger target volumes when applying target repaintings FIG. 6 show the typical changes in shape (narrowing of the width in depth) of the Bragg peak when the beam energy is changed to low energies

Under the assumption of repainting the dose several times (i.e. 10 times) the position of the patient table PT can be changed in smaller steps between repainted fields as shown in FIG. 5. By changing the position of the patient table PT very slowly the patient does not recognize its motion. The dose gradient of the cumulated in the interior of the field can be kept very low (about 50% of the dose per 8 cm≈6% per cm). The delivery of each partial-dose partial-volume field is done while moving slowly the patient table PT across the resulting large field. Pictorially, the dose distribution grows like in a moving sand dune. The gradients are so shallow that there does not occur any practical difference between this technique and the situation where the scan range in T- and U-direction is large enough to cover any assumed very large target volume.

FIG. 5 now depicts schematically this patching of fields for volumes larger than those directly accessible by only T- and U-sweeping with the second method of multiple target repaintings. Instead of delivering the same dose 8-times at the same position of the patient table PT the patient table is shifted continuously between the delivery of partial volumes. The volumes are painted (using the T-sweeper, the U-sweeper and the energy) according to a trapezoidal filter function applied to the T-sweeper motion to the required intensity of the beams spots (painted lines in FIG. 5). The dose filters are cumulated in connection with the slow movement of the patient table PT, which is moved once from the left to the right and back to the left. The control unit of the T-sweeper steers the beam B in a way that the motion of patient table is considered as an offset of the T-sweeper but offering "new" sub-volumes for painting on the leading edge of the patient table and loosing "old" sub-volumes on the trailing edge of the patient table PT as seen in the direction of the movement of the patient table PT.

Figure 6:
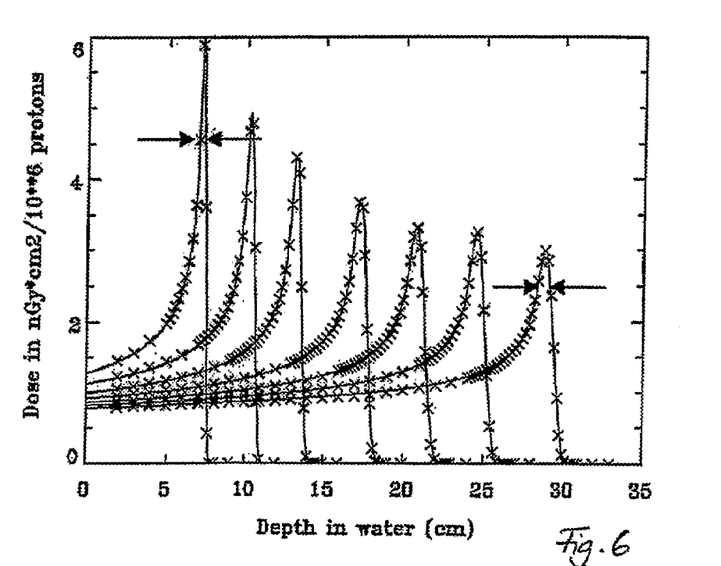

Very often the predetermined target volume is located close to the skin of a patient what requires a low range of the proton beam in the tissue. Unfortunately, low ranges of the protons may imply low beam energies, which have several drawbacks. At low energy most of the beam is lost in the degrader, the intensity of the beam becomes rapidly prohibitively low, even if one try to compensate for this by increasing the current extracted from the accelerator (this applies to using a cyclotron). A major drawback is the difficulty of designing a dose plateau in depth with the beam, since the beam becomes very sharp in depth at lower energy (the behavior is shown in FIG. 6). The task to deliver of a homogeneous Spread out Bragg peak (SOBP) using a reasonably small number of energy steps becomes prohibitively difficult.

This problem is shown in FIG. 6, where several Bragg peaks are plotted at different beam energy (using a momentum band of the transmitted beam which is representative for the state of this technique). The lower the energy of the beam is, the sharper is the width of the Bragg peak.

In order to avoid these drawbacks, a pre-absorber body may be optionally disposed between the outlet of the nozzle and the patient. Preferably, the pre-absorber body may comprise absorbing materials of low atomic number, to keep the broadening of the pencil beam due to Coulomb multiple scattering (MCS) in this material as low as possible. Through the use of such a pre-absorber the proton energy in the proton beam can be used within a rather high beam energy bandwidth enhancing also the stability of the proton beam. In addition, a dose plateau (according to spread out Bragg peak) can be designed starting closely under the skin in comparably lower depths.

The impact of a pre-absorber PA (FIG. 7) is setting a depth off-set. Therefore, the use of very low energy proton beams is avoided which in addition are both difficult to handle stable and show a very sharp Bragg peak making the low energy beams very sensitive to organ motion errors.

The use of a pre-absorber is a necessity for working with low proton ranges (if we disregard the use of complex moulds applied directly onto the patient skin), when we want to stop the beam at low ranges under the patient skin.

When such a pre-absorber block is inserted in the beam, this represents a significant amount of material in the beam, which inevitably scatters the protons through the physical process called Coulomb multiple scattering (MCS). This effect results in an unwanted broadening of the pencil beam width due to the use of the pre-absorber. The beam width increases linearly with the distance between pre-absorber and patient (linear propagation of MCS of the block in the air gap before the patient). The best strategy is therefore to keep the air gap as small as possible, preferably zeroed. The larger the air gap is, the bigger is the pencil beam width, the less precise is the lateral fall-off of the dose distribution and the more unsatisfactory is the quality of the treatment.

The major point to be considered in the design of the nozzle, is therefore to be able to place the patient as close as possible to the exit of the nozzle (near the pre-absorber). This must be possible for all considered beam directions. This is a major point acquired from the experience of using Gantry 1, a point, which is now most optimally realized on Gantry 2.

The patient shoulders pose a severe problem in this respect, especially when the patient is lying supine and the beam must be delivered horizontally on the left or right side of the head (as shown FIG. 4). The smaller is the space occupied by the nozzle, the better we can bring the patient head close to the pre-absorber.

Figure 7:
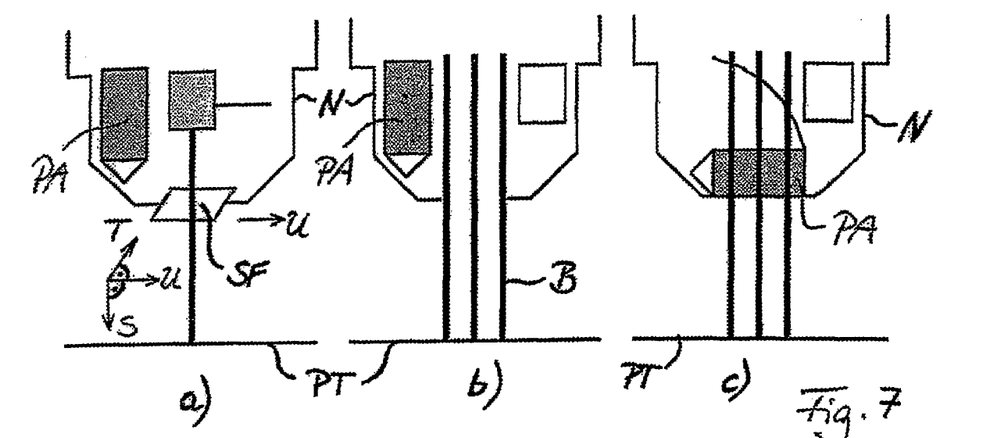
FIG. 7 is a principle use of a pre-absorber block in the nozzle.

We therefore aim of using a possibly small slim nozzle design. In FIG. 7 a) to c) the system design with respect to the pre-absorber PA is schematically illustrated. The pre-absorber PA is used to mimic human tissue in order to establish a spread out Bragg peak also very close under the skin of a patient without being forced to use comparably lower energies to shorten the beam range. Therefore, the drawbacks inherited from too small energies, namely weak beam stability, too low intensity and difficulties to design a spread out Bragg peak, are avoided. The pre-absorber body PA shifts the proton range back to the patient skin while using dynamic energies above 120 MeV. Additionally, the pre-absorber body PA may be machined with an embedded ridge filter to increase the width of the Bragg peak for a better homogeneity of the spread-out Bragg peak. While incorporating the pre-absorber body PA within the nozzle N, the principle layout of the nozzle N though having a rather smaller scan field region area SF in both directions T and U enroles now its main advantages because the patient can be placed very close to the outlet of the nozzle N. For that reason, the lateral broadening of the beam B due to multiple Coulomb scattering can be almost completely suppressed and the beam B maintains its sharpness thereby adjusting the true dose delivery close to the calculated dose gained from theoretical dose simulations.

The area scanned by the parallel beam should ideally correspond to only the lateral cross section of the nozzle. This problem is depicted in the FIG. 4, option B. In principle, one can argue that in theory one can position the head close to the edge of the nozzle N also with a bulky nozzle of a long throw gantry. This implies however that we are delivering the beam with the most tilted incidence on the patient.

The pre-absorber block is depicted in FIG. 4 for the two gantry types A (prior art) and B (inventive solution). If we have a long throw gantry A we are using a large preabsorber block $PA_A$ of the size of about 40 cm×50 cm with a weight of 20 kilograms. Since in most cases we want to deliver the proton beam—with and without block—in one and the same fraction, this block should be designed to be removable by motors from the beam.

At PSI, we have decided to accept a compromise, by using a rather limited range of magnetic scanning (10 cm×20 cm) since this allows the design of a very slim (permanently installed) small simple nozzle. The pre-absorber block $PA_B$ is then of the size of about 25 cm×15 cm, i.e. of only 4 kilograms. For the compactness of Gantry 2 (of the solution B type) we suggest to just tilt in and out the pre-absorber $PA_B$ plate in the beam by rotating it along its longer side. The space in the longitudinal beam direction occupied by the rotation is the short side of the block $PA_B$, which is only 15 cm.

If we would rotate in and out the 50 cm×40 cm pre-absorber block $PA_A$ for a long throw gantry in the same way we have to place the monitors at a larger distance from the patient. We would then have a less good knowledge from the monitors on the position of the beam impinging in the patient and we would increase the broadening of the beam due to the MCS in the monitors. If we would move the pre-absorber out laterally out of the beam we would increase the cross section of the nozzle, making it even more bulky.

A small nozzle appears to us for these practical reasons and for the comfort of the patient to be a better solution than a bulky nozzle. Innovative is here the compact arrangement for the motion of the pre-absorber block to keep the size of the nozzle small in all three dimensions.

By accepting a rather reduced range of magnetic scanning and by compensating this limitation with the geometrical patching technique described above, we can afford to use a nozzle having a very small cross section transverse to the beam. This is a more friendly solution to the patient for positioning him very close to the pre-absorber. In this way we can satisfy all given therapy conditions in the most optimal way.

We now describe in more details the scanning methods.

For the therapy of the target volume within a patient, two general known methods can be applied. A first method provides a "step and shot"-method while painting the total dose in one plane in depth (one energy step) by sweeping the beam B in both lateral directions T and U. The shifting of the Bragg peak in depth is performed in this method as the last frequent motion. Under the assumption of a target volume of 1 liter (10 cm×10 cm×10 cm) and a 7 mm FWHM on a 5 mm grid, approximately 21×21×21≈10,000 shots having an average duration of 10 ms have to be applied to the target volume that leads to approximately 100 seconds beam on time. Further, under the consideration of a given reaction time of the kicker of 50 µs, a dead time between the spots of about 2 ms and a dead time of either the U- or the T-sweeper of 1 s per plane and a dead time of the motion degrader of about 3 s (150 ms per plane times 21) the total dead time lays in the range of about 24 second per 10,000 shots allowing a scanning speed of 5,000 to 10,000 spots per minute.

The patient table PT will be only used for patching fields and/or for the correction of the positioning of the patient.

The second method is prosecuted by a continuous scanning with beam intensity modulation (a television-like mode). This method requires that the target volume is divided into isorange-layers of planes each having lines in the lateral U-or T-direction. These lines can be painted with continuous speed in the respective direction without switching off the beam B. The shape to the dose is thereby given by using the modulation of the intensity of the beam at the ion source within the cyclotron. The scanning in depth (the change from one isorange-layer to the other) is thereby again done by changing the energy of the proton beam B dynamically with the degrader. In this method, a liter of the target volume can be painted about 9 times per minute under the assumption that a line can be painted within 5 ms plus 3 ms for the step motion of the respective other sweeper. One plane having again a line structure with a grid of 5 mm leading to 21 line each requiring 8 ms to be painted. One plane therefore requires 168 ms plus 150 ms for the change of energy for the next plane which results at 318 ms for painting and, changing a plane. According to the 5 mm grid structure 21 energy steps are required that leads to 318 ms times 21=6.7 second for painting the complete target volume of 10 cm×10 cm×10 cm=1 liter volume.

It can be summarized that the time needed for changing the energy is comparable to the time needed for painting a plane of dose. The time required for painting the target volume once lays in the range of the respiration cycle of a person in idle status. Therefore, dose errors caused by organ motion can be middled out due to the possibility of multiple target painting within a comparably low period of time. Therefore, the required dose in each sub-volume of the target volume can be as well divided into sub-doses, which will be applied step by step within the repainting procedure of the target volume. Additionally, the scan strategy might further be optimized for example by less rescanning on the most proximal slices and more on the most distal layers, those which require most of the dose.

With this method the same quality of the dose distribution as with the first method can be achieved but with a factor 8 to 10 faster target repaintings. With this method it is possible to apply IMPT (intensity modulated proton therapy) also to moving targets by scanning the small pencil beam without the need to use collimators and compensators while maintaining the advantage of the small size of the nozzle N with the afore-mentioned features.

A very fast scan procedures provides a painting strategy with painting the two dimensional array line by line, whereby the intensity of the proton beam is modulated according to the desired target doses or partial target doses along the line. Therefore, the proton beam can be applied to the two-dimensional arrays comparable to the function of an electron beam of a cathode ray tube. The dead times of the proton beam per two-dimensional array of sub-volumes are therefore limited to only switching off the proton beam when changing the line.

Additional dead time only occur when changing the range of the proton beam in order to paint the subsequent two-dimensional array of sub-volumes. In total, this procedure enables the facility to be best suited for multiple three-dimensional target volume repainting within a time period comparable to the human idle respiration cycle. This performance supports tremendously the elimination of organ motion errors. Of course, the proton beam can be applied discontinuously within each line, which involves unfortunately on the other side longer dead time in-between the spots.

The method to adapt the dose by slowing down the beam motion of the sweeper magnets instead of changing dynamically the intensity is another easier but slower alternative method. As a new method is the procedure to scan the volume following the target contours and on equidistant contour at the interior of the target.

Option 1: Contoured Painting with Optional use of Beam Intensity Modulation

This mode of scanning has the following approaches:
- a.) Painting of the treatment volume in iso-energy layers (the Bragg peak covers with dose a layer at a depth equivalent to the range of the protons for the given beam energy). Such a layer is very efficiently conformally painted by double magnetic scanning.
- b.) Change of energy in between layers with beam off, by changing the setting of the degrader and the setting of the beam line elements in the section from the degrader to the patient.
- c.) Optionally, magnetic painting of a layer by scanning the beam along concentric target contours.
- d.) Optionally, control of the dose delivery during a contour painting by changing dynamically the beam intensity directly in the proton source.

Figure 8:
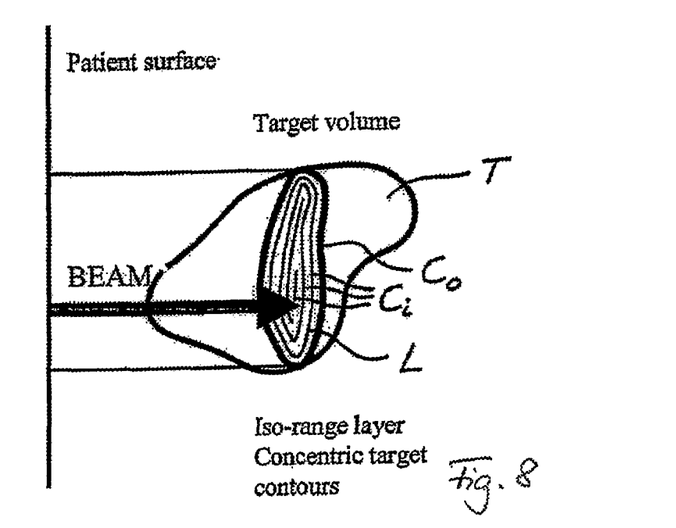
FIG. 8 is a schematic drawing to show the principle for applying an intensity modulated contoured scanning

FIG. 8 shows the principle. The method is based on the idea to scan the volume in energy layers L and lines as this is done on a television-like mode, but where the lines are painted along the beam-eye-view (BEV) contour of the target T at the depth corresponding to the given energy-layer and on similar equidistant contours in the inside of the target T. The beam shall be moved with close-to-maximum velocity and the painting of the dose will be achieved through modulation of the beam intensity using the deflector plate of the accelerator.

Figure 9:
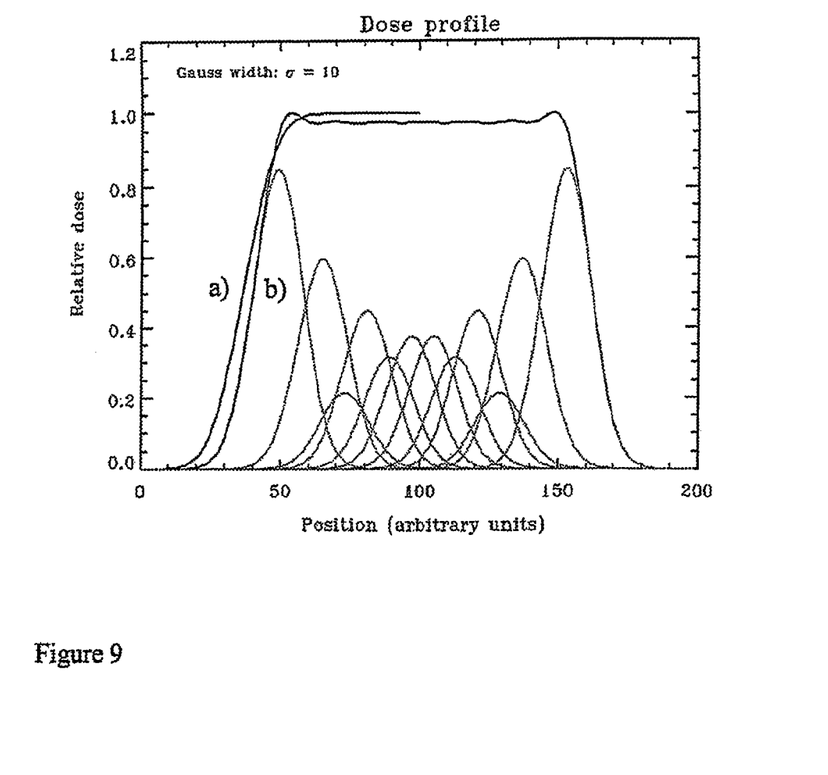
FIG. 9 is a diagram to show the lateral dose fall-off difference when the beam is scanned perpendicular or tangential to the target contour (see text later below).

To understand the difference to the previous scanning mode, we have to understand the factors affecting the lateral fall-off of the dose. We assume that the beam spot that we use is the one minimally available in the beam line to obtain the sharpest possible fall-off. FIG. 9 shows the difference in the lateral fall-off obtained through the addition of Gaussian beam spots for two typical cases.

In the case a) the beam spot profiles are added at separately spaced sparse discrete positions. Through the optimization algorithm in the dose calculation, by selecting the dosage of each contribution individually, one can obtain a good homogeneity of the dose on the inside of the target, while keeping the dose lateral fall-off to be essentially governed by the fall-off of a single constituent Gaussian.

If one deposit the same beam in a continuous mode (integrating it along a beam off-on-off rectangle) one obtains curve b).

The relative difference in the fall-off of the curves a) and b) is in the limiting case the difference between a Gauss function and the error-function (which is the folding of the original Gaussian with a step function). The difference in slope at the 50% level is 48%. From this we conclude that it is more convenient from the point of view of the precision of the dose distribution to place isolated beam spots in the direction perpendicular (surface normal) to the target contour.

If one uses the approach to scan along parallel beam lines (the television mode described above), the dose optimization algorithm will thus try to construct an intensity modulation profile which simulates as much as possible isolated sparse spots at the edge of the field. The intensity modulation will thus try to produce intensity patterns with very sharp dose peaks at the edge of the contour. The optimization will thus try to deliver a very high dose in a very short time. The system will thus be very demanding on the maximum dose rate and on the speed of changing the intensity (i.e. a very high beam intensity dynamics).

This behavior will be much relaxed if we pay the effort to scan both magnets along isocentric contour lines.

The method to follow contours shall provide the same amount of rescanning as with a television-like mode, but we expect with this method two possible major advantages:

1. By moving the beam tangentially along the contour we keep the lateral fall-off as sharply as possible as given by the original Gaussian shape of the beam, while needing a much lower dynamics of the beam intensity as compared with the mentioned television-mode. To achieve an edge enhancement effect as described above, we need to deliver almost separated single spots at the edge of the target if the beam is crossing the target contour. This would require the delivery of very high doses (at very high dose rate) in a very short time (high beam intensity dynamics). With the new contoured mode we are now able to obtain the same precision but with a much lower dynamics.
2. We expect that along the contours the required optimized dose will vary less rapidly as when we move the beam perpendicular to the edges of the field. The internal contours will probably require less dose than the one on the target boundary. We could therefore repeat the volumetric repainting more often on the external contours and less often in the inside of the target (i.e. to work with a more equalized beam intensity bandwidth in general).

Option 2: Broad Beam Contoured Scanning with "Imaged Collimation"

For this option we will use the same approach as above, but we will scan the beam at a somewhat slower speed and we will paint the dose with a much larger beam spot. The next idea is to have a collimator mounted at the coupling point of the gantry (the point on axis of the entrance into the rotating beam line). The collimator can be moved under motor control radially in-out and azimuthally around the beam axis as shown schematically on the left side of FIG. 10. The collimation effect applied to the beam at the entrance to the gantry (the beam optics source) is then imaged 1:1 on the scanned beam spot. We can therefore apply scanning with a large beam spot, while keeping the lateral fall-off very sharp (the spot gets clipped at the boundary to the target).

Figure 10:
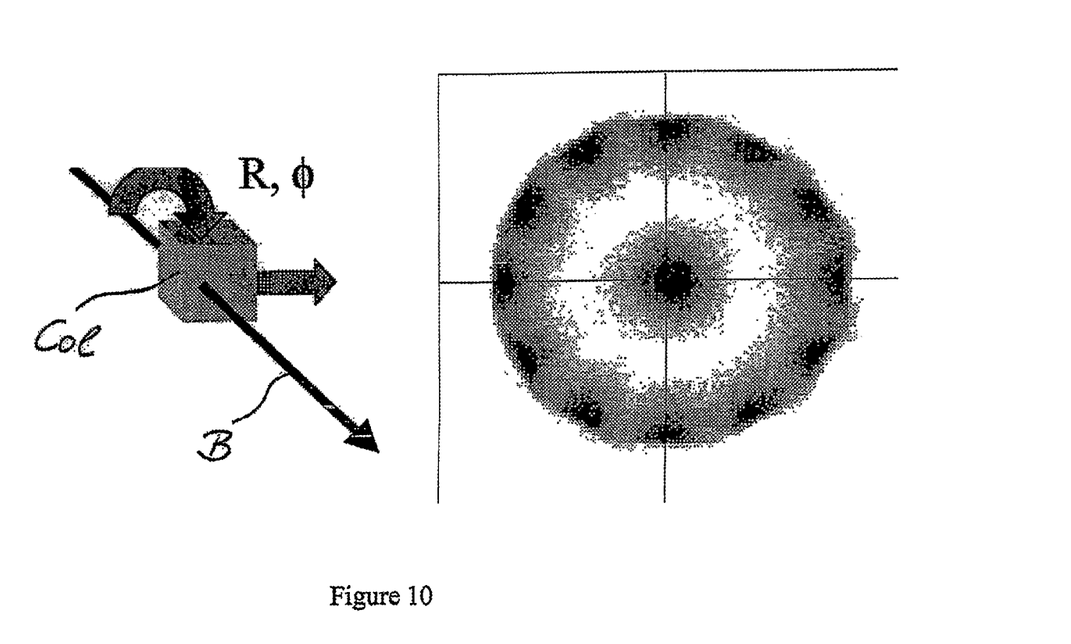
FIG. 10 is a diagram to show the functional concept of a motorized collimation block placed at the entrance of the gantry (on the left side—schematics of a block moving radially and azimuthally around the beam axis). The right side is a Monte Carlo simulation showing the effect of an imaged collimation on the beam transported through and scanned at the end of the gantry.

The method is in principle available in view of the proposed beam optics, which is a 1:1 image from the coupling point of the gantry to the isocenter. While the beam follows the target contour, the collimator at the coupling point will be moved into the beam and will be rotated for the cut to remain tangential to the virtually imaged target contour. In this way it is possible to obtain a sharp lateral fall-of the dose while scanning an inherently broad beam.

FIG. 10 shows on the right the result of a Monte Carlo simulation applied for a proof of principle to a circle as the target. The beam spot images at the isocenter show the effect of the collimator imaged from the coupling point to the gantry.

The use of a remotely controlled collimator could be thus used to produce sharp dose edge boundaries while using large beams, i.e. to obtain the same effect as by using an individually shaped collimator placed just before the patient. By scanning with a broad beam we will avoid depositing sharp dose gradients at the interior of the target. This method is therefore quite robust against organ motion problems. By using a broad beam we can gain in capability of repainting (coarser grid—shorter path—more repainting), especially at the interior of the target, where can run with a higher speed (when the collimator is radially fully retracted). The result should be quite similar as a beam delivery with a passive scattering technique, but with the advantage that there is no need to fabricate individually shaped apertures and no need to mount additional equipment on the nozzle for each field.

The new method could however suffer from MCS in the monitors, spoiling the quality of the lateral fall-off of the dose especially at low energy.

The design of an overall beam delivery system for proton therapy capable of satisfying different clinical requirements all at once is a difficult optimization exercise.

One has to provide:

automated conformal fast dose delivery to apply multiple fields in a sequence, with good homogeneity of the dose and with a sharp lateral and distal fall-off, dose delivery to any depth in the body and to any possible target size, freedom in a 4π solid angle for the use of multiple beam directions applied on the immobilized supine patient, small air gap, short treatment time, multiple target repaintings to cope with organ motion, possibly small compact gantry design.

These contradictory requirements are in our opinion conceptually well satisfied in our design all at once, which is a significant achievement.

The availability of both modes, fast contoured scanning with a small beam or slower contoured scanning with imaged collimated varying (small or large) beams, should bring the scanning technique close to its maximum possible performance, to the maximum benefit to the patients. These advanced beam scanning techniques applied on the optimized nozzle design described in the first part, should provide one of the most performing systems of the world.

The invention claimed is:

1. A system for an intensity-modulated proton therapy of a predetermined volume within an object, the system comprising:
   a) a proton source for generating a proton beam being adjustable with respect to beam intensity;
   b) a degrader being optionally disposed in the proton beam for attenuating energy of protons in the proton beam to a desired proton energy in the proton beam;
   c) a beam transport system being supported by a support frame pivotable around an optical axis; said beam transport system including:
   d) a plurality of proton beam bending and/or focusing units;
   e) a beam nozzle having an outlet for the proton beam for penetrating a predetermined volume of the object;
   f) a beam bending magnet being disposed upstream of said nozzle; and
   g) a couple of sweeper magnets being disposed upstream of said beam bending magnet for sweeping the proton beam in both lateral directions before the proton beam enters into said beam bending magnet,
   h) said beam nozzle defining a cross-sectional scanning area substantially perpendicular to the proton beam in the range of 10 cm×30 cm, and
   i) said sweeper magnets and said beam bending magnet being controlled to substantially provide a parallel beam orientation over a complete cross-sectional scanning area and for delivering a substantially 1:1 beam image of the proton beam before entering into said beam bending magnet as compared to the beam image after the bending.

2. The system according to claim 1, wherein a preabsorber body is optionally disposed between the outlet of the nozzle and the object.

3. The system according to claim 1, wherein the cross-sectional scanning area is oriented substantially perpendicular to a longitudinal axis of the proton beam, and a moving mechanism for the preabsorber body is provided which is remotely controllable to move the preabsorber body from a parking position into an absorbing position to cover the complete scanning area.

4. The system according to claim 2, wherein the preabsorber body comprises at least one of carbon and beryllium.

5. The system according to claim 1, wherein a collimator is optionally pivoted into the proton beam upstream of the beam bending magnet; said collimator being movable radially and/or azimuthally.

6. The system according to claim 1, wherein the object is supported by a table which is optionally movable in a plane being substantially perpendicular to the proton beam by a table driving unit, whereby the movement of the table is detected by the table driving unit to control a deflection of the proton beam in a respective sweeper magnet for annihilating a relative shift between the object and the proton beam during dose painting.

7. A process for an intensity-modulated proton therapy of a predetermined volume within an object; comprising the steps of:
   a) discretising the predetermined volume into a number of iso-energy layers each corresponding to a determined energy of the proton beam;
   b) determining a final target dose distribution for each iso-energy layer; and
   c) applying at least a predetermined part of the final target dose distribution by parallel beam scanning by controlling respective beam sweepers thereby for scanning one iso-energy layer after the other using an intensity-modulated proton beam while scanning a predetermined iso-energy layer.

8. The process according to claim 7, including the step of multiple painting of the respective iso-energy layers, so that each painting delivers a predetermined part of the final target dose distribution.

9. The process according to claim 7, including the step of geometrically field patching by moving a support table continuously, thereby simultaneously compensating the displacement of the motion of the support table with an offset applied to the beam sweepers.

10. The process according to claim 7, including the step of magnetically scanning at each iso-energy layer along the contour of a target volume and on similar equidistant contours in an interior of the target volume, thereby shaping the dose by using beam intensity modulation along the contours.

11. The process according to claim 7, including the step of applying imaged collimation on the scanned beam by using a collimator block being radially and/or azimuthally moved into the proton beam at a coupling point of a beam transport system.

12. The process according to claim 7, including the step of controlling the beam sweepers and beam bending magnet to substantially provide a parallel beam orientation over a complete cross-sectional scanning area and to deliver a substantially 1:1 beam image of a proton beam before entering into the beam bending magnet as compared to the beam image after the bending.

* * * * *